US00PP08832P

United States Patent [19]

Frazer

[11] Patent Number: Plant 8,832

[45] Date of Patent: Jul. 12, 1994

[54] DIEFFENBACHIA PLANT NAMED TROPIC MARIANNE

[75] Inventor: Edwin J. Frazer, Queensland, Australia

[73] Assignee: Twyford International, Inc., Santa Paula, Calif.

[21] Appl. No.: 108,192

[22] Filed: Aug. 18, 1993

[51] Int. Cl.[5] ..... A01H 5/00

[52] U.S. Cl. ..... Plt./88.2

[58] Field of Search ..... Plt. 88.2

*Primary Examiner*—James R. Feyrer

*Attorney, Agent, or Firm*—Foley & Lardner

[57] ABSTRACT

A Dieffenbachia plant named Tropic Marianne, particularly characterized by its yellow-green oblong leaves bordered with green, and dense upright branched habit.

1 Drawing Sheet

The present invention comprises a new and distinct cultivar of Dieffenbachia, botanically known as *Dieffenbachia hybrida,* and referred to by the cultivar name Tropic Marianne.

The new cultivar is a product of a planned breeding program carried out by the inventor Edwin J. Frazer in Brisbane, Australia. The new cultivar is a product of a cross made between the following:

Pollen parent: Unnamed hybrid of Dieffenbachia Marianne × *Dieffenbachia hoffmanii.*

Seed parent: Unidentified Dieffenbachia species; Missouri Botanical Gardens accession No. MGB-7370801.

The cultivar was discovered from the progeny of the stated cross by Edwin J. Frazer in Brisbane, Australia. Asexual propagation by tissue culture by the inventor in Brisbane, Australia, increased the number of plants for evaluation and has demonstrated the stability of the combination of characteristics of Tropic Marianne from generation to generation.

The following observations, measurements and values describe plants grown in Zolfo Springs, Fla. under greenhouse conditions which closely approximate those generally used in horticultural practice.

The following traits have been repeatedly observed and are determined to be basic characteristics of Tropic Marianne, which in combination distinguish Tropic Marianne from other Dieffenbachia of the same general type, for example the well known cultivar Camille.

1. The leaves are larger, wider and thicker than those of Camille.
2. The leaves have darker green borders than Camille.
3. The plant has fewer branches than Camille.
4. The plant habit is dense and upright.
5. The plant is larger than Camille.

Color references below are to The Royal Horticultural Society Colour Chart. Colors may vary somewhat depending on horticultural practices such as light level and fertilization rate, among others, without, however any variance in genotype.

The color photographic drawing comprises a top perspective view of Tropic Marianne. The photograph is of a single plant of Tropic Marianne in a 15.3 cm pot approximately 28 weeks after planting a 12 week old liner obtained by tissue culture and grown under appropriate growing conditions. Colors are as accurate as possible with color illustrations of this type.

Origin: Seedling selected from a cross of:

*Pollen parent.*—Dief. 'Marianne' × *Deif. hoffmanii.*

*Seed parent.*—Unidentified Dieffenbachia species, Missouri Botanical Gardens accession No. MGB-7370801.

Classification: Dieffenbachia hybrida c.v. Tropic Marianne.

Propagation: Asexual production either by tissue culture or division.

Plant: In a 15.4 cm pot for a plant grown from a 12 week old liner after 28 weeks under appropriate growing conditions, Tropic Marianne will be approximately 12.5 cm to 15.5 cm, measured from the soil surface to the junction of the petioles of the last two (2) unrolled leaves, and approximately 29 cm to 37 cm in width.

Stem:

*Growth pattern.*—The stem is approximately 1.9 cm to 2.3 cm in diameter five (5) cm above the soil surface. Internode distance is approximately 1.2 cm to 1.5 cm above the soil.

Color.—137B in color.

Petiole: The following information is based on the 2nd expanded leaf from the apex.

*Growth pattern.*—The petiole has fleshy edges (wings) extending from the midrib. The wings are approximately 9 mm to 12 mm wide one-half (½) the distance from the petiole base to the wing apex. The wings extend from the base of the petiole to within approximately 1.2 cm to 1.5 cm of the base of the leaf. The apex of the wings is emarginate. The petiole follows the stem axis but diverges from the axis approximately 6.4 cm to 7.0 cm from the leaf base, forming a horizontal distance from the edge of the stem to the leaf base of approximately 1.5 cm to 1.7 cm.

*Dimensions.*—The petiole is straight from its base to the base of the leaf. The petiole is approximately 6 mm in diameter one-half the distance between the top of the wing and the base of the leaf, and approximately 8.1 cm to 8.5 cm in length.

*Color.*—The petiole and petiole wings are 137B in color; the midbrib is slightly lighter than the petiole.

Leaf:

*Growth pattern.*—The leaf is oblong with a cuspidate apex and an obtuse base. The margin is entire. The leaf is asymmetric with the side of the leaf unrolling first having less surface area than the side unrolling last. The leaf is oriented parallel to the stem axis at the time of full unrolling, changing to approximately 60 degrees above perpendicular to the stem axis as more leaves unroll above it. The midrib is straight over the length of the leaf. The leaf blade is flat from the midrib to the margin, drooping slightly near the edge.

*Dimensions.*—For the pot size and growing time indicated, the largest leaf is approximately 21 cm to 22.5 cm long and approximately 12 cm to 12.5 cm wide. An average sized leaf is approximately 16 cm to 19 cm long and approximately 10 cm to 11.5 cm wide. The leaf is moderately thick.

*Midrib.*—The midrib is thick and prominent.

*Primary veins.*—The primary veins are sunken into the upper surface and protrude out of the underside. The primary veins are the same color as the leaf tissue surrounding them.

*Color and pattern.*—The top surface of the mature leaf has a midrib color greener than 155A, becoming 137D near the base of the leaf, and a leaf blade color of 150C. The color changes to greener than 139A within approximately 15 mm to 20 mm of the edge of the leaf. The bottom surface of the leaf has a midrib color of 146C. The primary veins are 150D. The leaf blade color is 145C changing to 137B-C at approximately 15 mm to 20 mm from the leaf margin.

Axillary breaks: There are approximately 6 to 9 axillary breaks with at least one leaf expanded. Leaves will show color by the second leaf and will have true color and pattern by the third leaf.

Inflorescence: Typical of Dieffenbachia and does not have commercial significance.

Roots: Thick white roots with fine laterals.

General observations: Dieffenbachia Tropic Marianne has oblong yellow-green leaves bordered with green. The plant habit is branched, dense and upright. These combined characteristics make Tropic Marianne a unique new cultivar.

I claim:

1. A new and distinct cultivar of Dieffenbachia plant named Tropic Marianne, as illustrated and described.

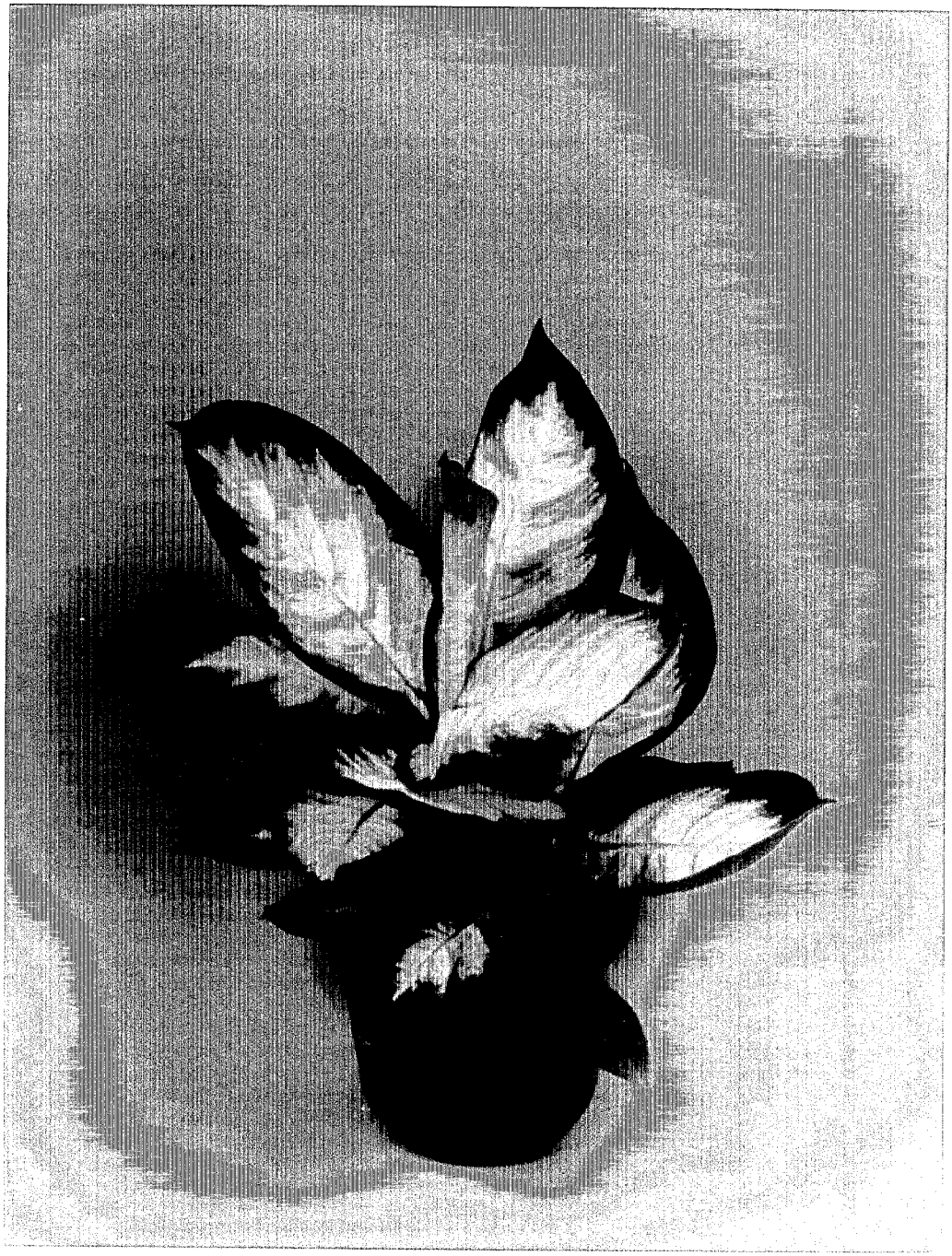

* * * * *